(12) United States Patent
Verkade et al.

(10) Patent No.: US 10,463,523 B2
(45) Date of Patent: *Nov. 5, 2019

(54) HINGED ANKLE BRACE

(71) Applicant: DJO, LLC, Vista, CA (US)

(72) Inventors: Drew R. Verkade, Carlsbad, CA (US); Jeremy Nathanson, San Clemente, CA (US); David Rodwell Walters, III, Columbia, SC (US)

(73) Assignee: DJO, LLC, Vista, CA (US)

( * ) Notice: Subject to any disclaimer, the term of this patent is extended or adjusted under 35 U.S.C. 154(b) by 554 days.

This patent is subject to a terminal disclaimer.

(21) Appl. No.: 15/179,806

(22) Filed: Jun. 10, 2016

(65) Prior Publication Data

US 2017/0000640 A1 Jan. 5, 2017

Related U.S. Application Data

(63) Continuation of application No. 13/851,725, filed on Mar. 27, 2013, now Pat. No. 9,364,366, which is a (Continued)

(51) Int. Cl.
*A61F 5/00* (2006.01)
*A61F 5/01* (2006.01)

(52) U.S. Cl.
CPC .......... *A61F 5/0127* (2013.01); *A61F 5/0111* (2013.01); *A61F 2005/0137* (2013.01); *A61F 2005/0172* (2013.01)

(58) Field of Classification Search
CPC .................. A63C 2203/50; A63C 9/002
(Continued)

(56) References Cited

U.S. PATENT DOCUMENTS 1,381,290 A 6/1921 Diadul, Jr.
3,064,644 A 11/1962 Patterson
(Continued)

FOREIGN PATENT DOCUMENTS

AU 37277/93 9/1993
EP 0619102 10/1994
(Continued)

*Primary Examiner* — Kim M Lewis
(74) *Attorney, Agent, or Firm* — Veros Legal Solutions, LLP

(57) ABSTRACT

A hinged ankle brace having a semi-rigid ankle cuff and a semi-rigid foot bed rotatably connected by a medial hinge and a lateral hinge provides enhanced stability and support to a wearer's ankle. The medial hinge of the ankle brace may be higher than the lateral hinge to accurately replicate the bending motion of an ankle. The ankle brace also includes ratchetably interconnected semi-rigid straps. These semi-rigid straps provide a semi-rigid structure encircling the ankle of a wearer for enhanced support. The ratchet mechanism may include a curved window that enables angular adjustment of the ratcheting straps. The ankle brace may also include a soft inner liner and a soft outer sleeve. The outer sleeve is configured to provide compression to the semi-rigid shell, which in turn provides additional compression to the ankle. The semi-rigid foot bed may include posterior extensions that cup and support the wearer's heel, and a posterior cut-out portion that receives the wearer's heel.

12 Claims, 15 Drawing Sheets

Related U.S. Application Data continuation of application No. 11/243,754, filed on Oct. 4, 2005, now Pat. No. 8,641,654.

(60) Provisional application No. 60/615,621, filed on Oct. 4, 2004.

(58) Field of Classification Search
    USPC .......................................................... 602/27
    See application file for complete search history.

(56) References Cited

U.S. PATENT DOCUMENTS

| | | | |
|---|---|---|---|
| 3,363,270 A | 1/1968 | McClive | |
| 3,674,023 A | 7/1972 | Mann | |
| 4,280,488 A | 7/1981 | Polsky et al. | |
| 4,280,489 A | 7/1981 | Johnson, Jr. | |
| 4,446,856 A | 5/1984 | Jordan | |
| 4,497,070 A | 2/1985 | Cho | |
| 4,510,927 A | 4/1985 | Peters | |
| 4,517,968 A | 5/1985 | Greene et al. | |
| 4,628,945 A | 12/1986 | Johnson, Jr. | |
| 4,646,726 A | 3/1987 | Westin et al. | |
| 4,651,726 A | 3/1987 | Holland | |
| 4,665,904 A * | 5/1987 | Lerman | A61F 5/0127 16/221 |
| 4,724,847 A | 2/1988 | Nelson | |
| 4,776,111 A | 10/1988 | Crowley | |
| 4,825,856 A | 5/1989 | Nelson | |
| 4,834,078 A | 5/1989 | Biedermann | |
| 4,865,023 A | 9/1989 | Craythorne et al. | |
| 4,934,355 A | 6/1990 | Porcelli | |
| RE33,395 E | 10/1990 | Peters | |
| 4,966,134 A | 10/1990 | Brewer | |
| 4,977,891 A | 12/1990 | Grim | |
| 5,031,607 A | 7/1991 | Peters | |
| 5,050,620 A | 9/1991 | Cooper | |
| 5,088,478 A | 2/1992 | Grim | |
| D326,719 S | 6/1992 | Eghamn | |
| 5,125,400 A | 6/1992 | Johnson, Jr. | |
| 5,177,884 A | 1/1993 | Rullier | |
| 5,209,722 A | 5/1993 | Miklaus et al. | |
| 5,217,431 A | 6/1993 | Toronto et al. | |
| D338,066 S | 8/1993 | Baron | |
| 5,242,379 A | 9/1993 | Harris et al. | |
| 5,331,752 A | 7/1994 | Johnson et al. | |
| 5,348,530 A | 9/1994 | Grim et al. | |
| 5,366,439 A | 11/1994 | Peters | |
| 5,445,602 A | 8/1995 | Grim et al. | |
| 5,501,659 A | 3/1996 | Morris et al. | |
| 5,613,941 A | 3/1997 | Prengler | |
| 5,676,642 A | 10/1997 | Peters | |
| 5,735,805 A | 4/1998 | Wasserman et al. | |
| D394,112 S | 5/1998 | Duback et al. | |
| 5,778,563 A | 7/1998 | Ahlbaumer | |
| 5,795,316 A | 8/1998 | Gaylord | |
| 5,797,865 A | 8/1998 | McDavid, III | |
| 5,836,903 A * | 11/1998 | Peters | A61F 5/0127 602/27 |
| 5,853,381 A | 12/1998 | Stevenson et al. | |
| 2,766,359 A | 1/1999 | Cermolacce et al. | |
| 5,868,693 A | 2/1999 | Duback et al. | |
| 5,902,259 A | 5/1999 | Wilkerson | |
| 5,951,504 A | 9/1999 | Iglesias et al. | |
| 5,971,946 A | 10/1999 | Quinn et al. | |
| 6,024,712 A | 2/2000 | Iglesias et al. | |
| 6,126,625 A | 10/2000 | Lundberg | |
| 6,350,246 B1 | 2/2002 | De Toro et al. | |
| 6,398,750 B1 | 6/2002 | Quinn et al. | |
| 6,689,081 B2 | 2/2004 | Bowman | |
| 6,858,017 B2 | 2/2005 | Peters | |
| 6,964,663 B2 | 11/2005 | Grant et al. | |
| 8,641,654 B2 * | 2/2014 | Verkade | A61F 5/0127 602/23 |
| 9,364,366 B2 * | 6/2016 | Verkade | A61F 5/0127 |
| 2001/0056251 A1 * | 12/2001 | Peters | A61F 5/0127 602/27 |
| 2002/0173739 A1 | 11/2002 | Jensen | |
| 2004/0034316 A1 * | 2/2004 | Castro | A61F 5/0111 602/27 |

FOREIGN PATENT DOCUMENTS

| | | |
|---|---|---|
| FR | 2766359 | 1/1999 |
| WO | WO/1993/006797 | 4/1993 |

* cited by examiner

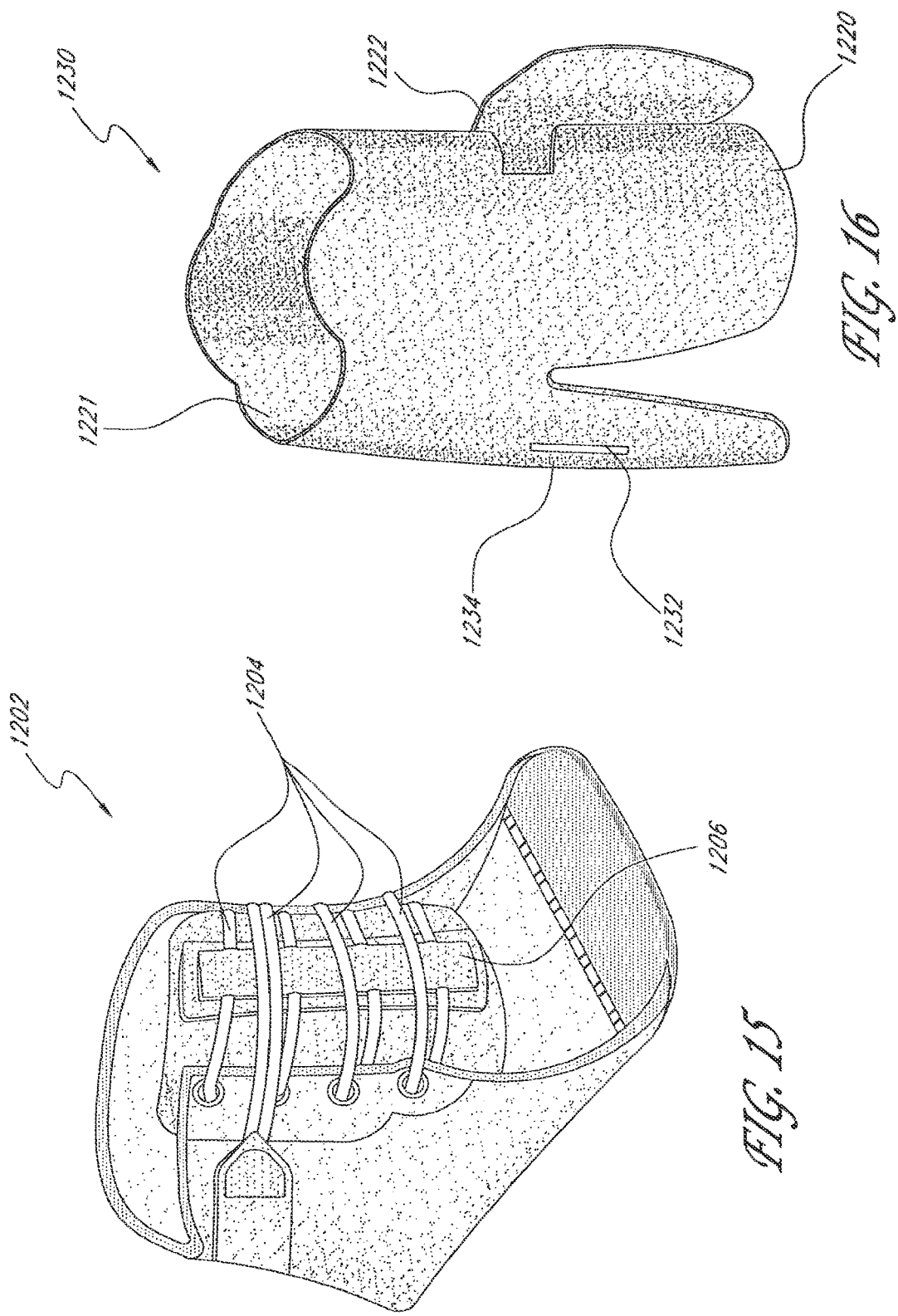

HINGED ANKLE BRACE

CROSS-REFERENCE TO RELATED APPLICATIONS

This application is a continuation of co-pending U.S. patent application Ser. No. 13/851,725, filed Mar. 27, 2013, which is a continuation application of and claim priority to U.S. patent application Ser. No. 11/243,754, filed on Oct. 4, 2005 and now issued as U.S. Pat. No. 8,641,654, on Feb. 4, 2014, which claims priority to U.S. Provisional Application Ser. No. 60/615,621, filed Oct. 4, 2004, and each application is hereby incorporated by reference in their entireties.

BACKGROUND OF THE INVENTION

Field of the Invention

The present invention relates to orthopedic ankle braces.

Description of the Related Technology

A variety of ankle braces are currently available to prevent ankle injuries, such as sprains. Some braces include purely soft components, and others incorporate rigid components. In general, these braces are designed to support the wearer's ankle and prevent unnatural movements that might cause injury.

SUMMARY

The preferred embodiments of the present ankle braces have several features, no single one of which is solely responsible for their desirable attributes. Without limiting the scope of these ankle braces as expressed by the claims that follow, more prominent features will now be discussed briefly. After considering this discussion, and particularly after reading the section entitled "Detailed Description of the Preferred Embodiments," one will understand how the features of the preferred embodiments provide advantages, which include support for high ankle sprains, improved inversion and eversion control, reduced foot slippage, calcaneus support, and incremental adjustability as well as enhanced comfort, support and stability for a wearer.

In certain embodiments, the present ankle braces comprise a semi-rigid ankle cuff, a semi rigid foot bed, a medial hinge, and a lateral hinge. The semi-rigid ankle cuff includes a calf-supporting portion configured to extend around a posterior side of a lower calf of a wearer, a medial upright extending generally downward from a medial side of the calf-supporting portion, and a lateral upright extending generally downward from a lateral side of the calf-supporting portion. The foot bed includes a foot plate contoured to underlie at least a portion of a foot of the wearer, a medial wing extending generally upward from the medial side of the foot bed, and a lateral wing extending generally upward from the lateral side of the foot bed. The medial hinge rotatably connects the medial wing with the medial upright. The lateral hinge rotatably connects the lateral wing with the lateral upright. The medial hinge is positioned higher than the lateral hinge relative to the foot plate. Advantageously, this relative positioning of the medial hinge and the lateral hinge closely simulates ankle anatomy, thus allowing a natural bending motion of a wearer's ankle.

In other embodiments, the present ankle brace comprises a semi-rigid ankle cuff and a semi rigid foot bed. The semi-rigid ankle cuff includes a calf-supporting portion configured to extend around a posterior side of a lower calf of a wearer, a medial upright extending generally downward from a medial side the calf-supporting portion, and a lateral upright extending generally downward from a lateral side of the calf-supporting portion. The semi rigid foot bed includes a foot plate contoured to underlie at least a portion of a foot of the wearer, a cut out portion configured to receive a heel of a wearer, a medial wing extending generally upward from a posterior medial edge of the foot plate, and a lateral wing extending generally upward from a posterior lateral edge of the foot plate. The foot bed is rotatably coupled to the ankle cuff.

In other embodiments, the present ankle brace comprises a semi-rigid ankle cuff and a semi-rigid foot bed rotatably coupled to the ankle cuff. The semi-rigid cuff comprises a calf-supporting portion configured to support a posterior side of an ankle of a wearer, and at least one semi-rigid strap extending from the calf-supporting portion and including a ratchet mechanism to adjustably position the ankle cuff on the ankle of a wearer.

In other embodiments, the present ankle brace comprises a semi-rigid shell configured to overlie and support at least a portion of a wearer's ankle and/or foot, and an outer sleeve configured to overlie at least a portion of the semi-rigid shell, and configured to apply compression to the semi-rigid shell.

In other embodiments, the present ankle brace comprises a semi-rigid ankle cuff configured to overlie and support at least a portion of a calf and/or ankle of the wearer, and a semi-rigid foot bed configured to underlie at least a portion of the wearer's foot. The foot bed includes at least one of a medial posterior extension and a lateral posterior extension. The at least one posterior extension is configured to cup and support a heel of the wearer.

In other embodiments, a method for applying an ankle brace is provided. The method comprises the steps of applying an inner liner to the ankle of the wearer, applying a semi-rigid shell including an ankle cuff and at least one strap to the inner liner, incrementally adjusting the circumference of the ankle cuff, and securing the strap with respect to the calf-supporting portion. The semi-rigid shell comprises a foot bed and an ankle cuff rotatably coupled to the foot bed, the ankle cuff comprising a calf-supporting portion, at least one semi-rigid strap extending from the calf-supporting portion, and a ratchet mechanism to incrementally adjust a circumference of the ankle cuff.

In other embodiments, another method for applying an ankle brace is provided. The method comprises the steps of applying a semi-rigid shell to the ankle, securing the semi-rigid shell about the ankle, applying an outer sleeve over the semi-rigid shell, and securing the outer sleeve with respect to the semi-rigid shell. The semi-rigid shell includes structure that overlies and supports at least a portion of the ankle, and the outer sleeve is configured to overlie and compress at least a portion of the semi-rigid shell.

BRIEF DESCRIPTION OF THE DRAWINGS

The preferred embodiments of the present ankle braces, illustrating their features, will now be discussed in detail. These embodiments depict the novel and non-obvious ankle braces shown in the accompanying drawings, which are for illustrative purposes only. These drawings include the following figures, in which like numerals indicate like parts:

FIG. 15 is a front perspective view of an outer sleeve of the hinged ankle brace of FIG. 14; and FIG. 16 is a rear perspective view of an inner liner of the hinged ankle brace of FIG. 14.

DETAILED DESCRIPTION OF CERTAIN INVENTIVE EMBODIMENTS

Figure 1:
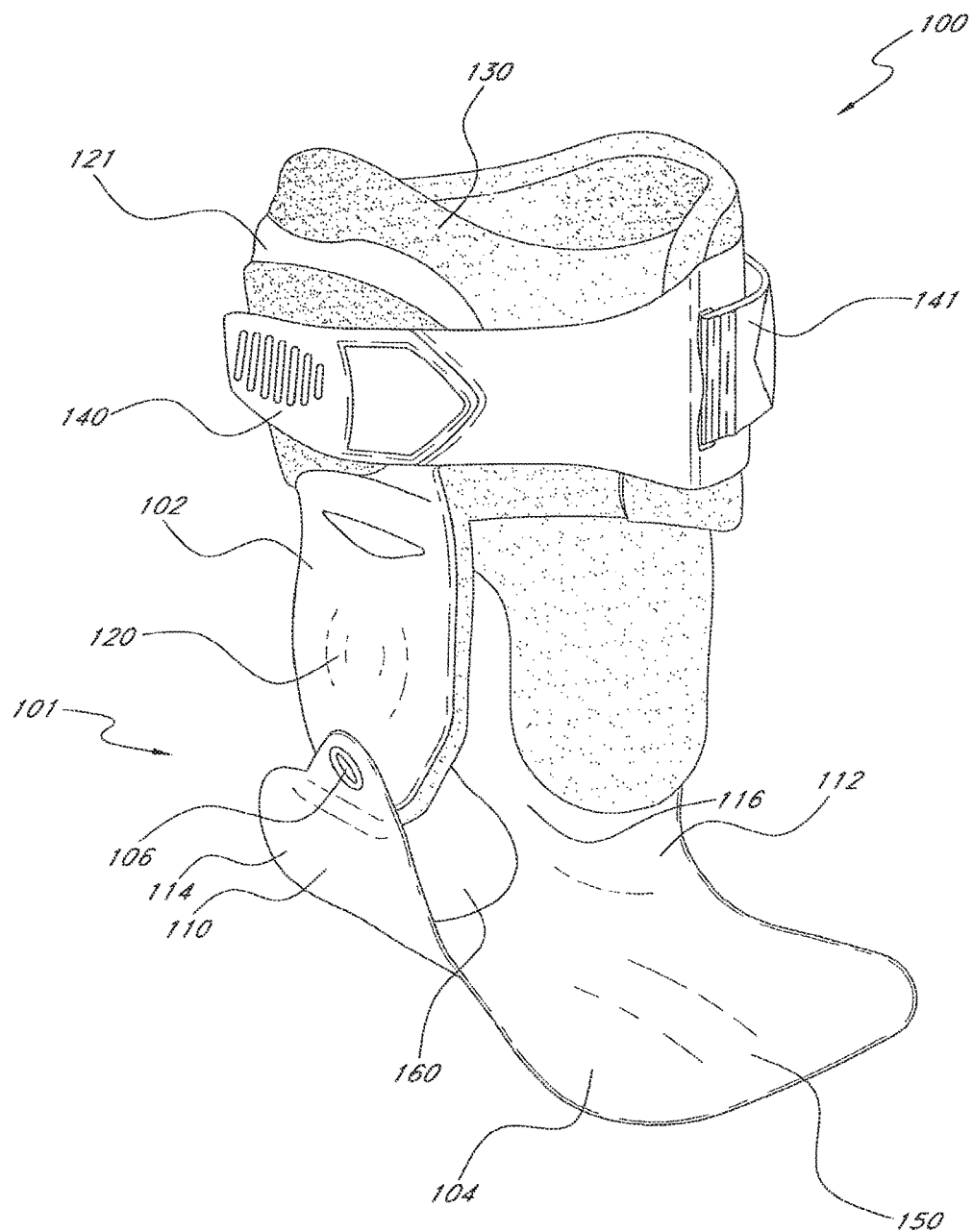
FIG. 1 is a front perspective view of a preferred embodiment of the present hinged ankle brace.

With reference to FIGS. 1-10, one embodiment of the present hinged ankle brace 100 includes a semi-rigid shell 101. The shell 101 comprises an upper ankle cuff 102 and a lower foot bed 104. In one embodiment, the lower foot bed 104 and the upper ankle cuff 102 are each constructed of a plastic material, such as polyamide or a composite of polyamide and ABS. The material used to construct the lower foot bed 104 and the upper ankle cuff 102 preferably imparts these components with semi-rigid characteristics, such that they generally hold their respective shapes and provide support to the wearer's ankle, but are capable of being deformed to match the contours of the wearer's ankle and to allow the wearer's ankle to follow its natural motion. Those of skill in the art will appreciate that any materials having the desired properties could be used to construct the lower foot bed 104 and the upper ankle cuff 102, and that the examples provided above are not limiting.

With reference to FIGS. 1-16, the illustrated embodiments of present ankle brace 100, 200, 300 are configured to fit a wearer's right ankle. However, those of ordinary skill in the art will appreciate that the configuration of the illustrated ankle braces could be reversed to provide an ankle brace configured to fit a wearer's left ankle. Moreover, certain features and aspects of the illustrated embodiments discussed further below, including the ratchetably interconnected straps and the outer soft sleeve, could be used in conjunction with a universal ankle brace, that is, one that is configured to fit either a wearer's left or right ankle.

As described in more detail below, in certain embodiments the hinged ankle brace comprises a three-layer apparatus including an outer soft sleeve 902, 1202 (FIGS. 11, 14), an inner soft liner 130, 1230 and a semi-rigid shell 101 disposed between the outer sleeve 902, 1202 and the inner liner 130, 1230. In certain embodiments, the hinged ankle brace is configured to be worn inside a shoe. The semi-rigid shell 101 provides sufficient flexibility to conform to a wearer's anatomy, but is sufficiently rigid to resist torsional distortion imparted by inversion and eversion forces. The ankle brace may be used for a variety of purposes including, but not limited to, prevention of ankle/foot rolling, protection against high ankle sprains, and protection against excessive supination and/or pronation of the foot.

Figure 2:
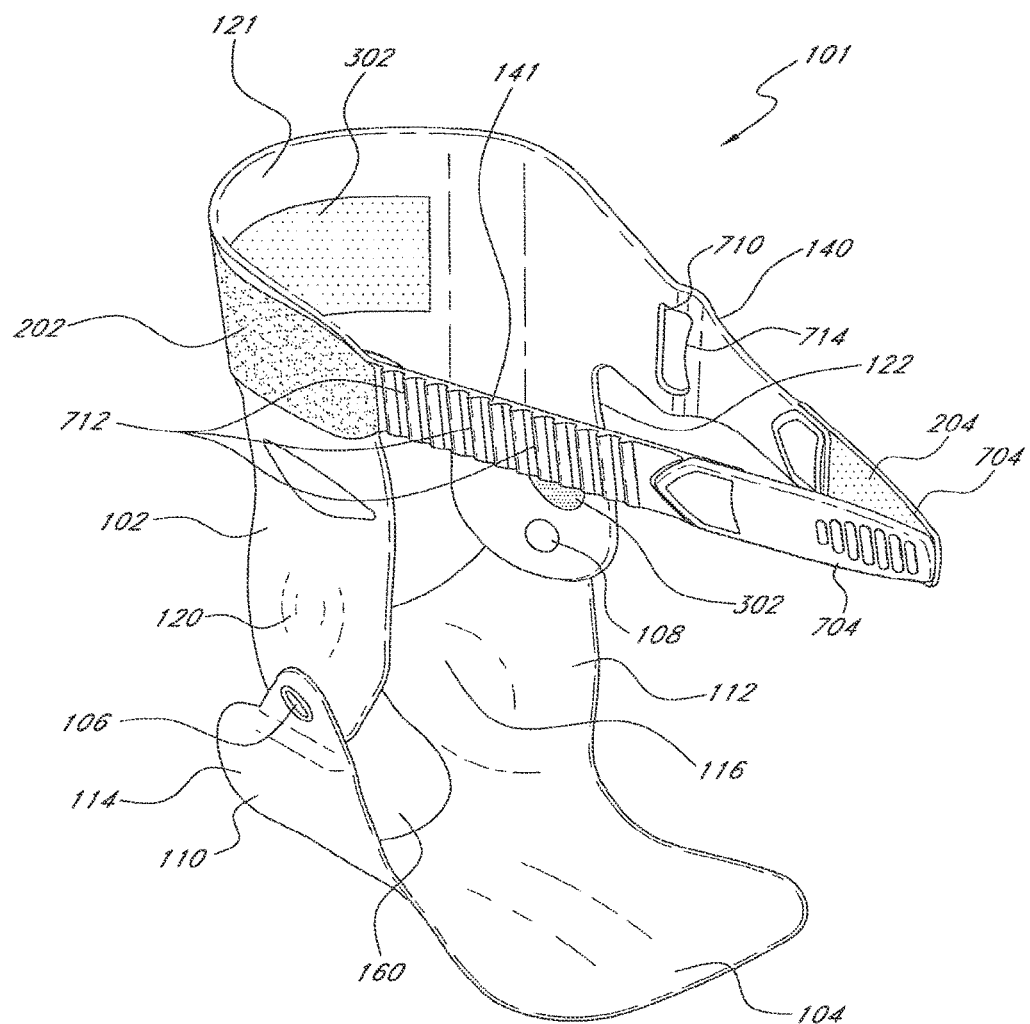
FIG. 2 is a front perspective view of a semi-rigid shell of the hinged ankle brace of FIG. 1, illustrating the semi-rigid straps of the shell in a disengaged configuration.

With reference to FIG. 2, one embodiment of the semi-rigid shell 101 comprises an ankle cuff 102 and foot bed 104, wherein the ankle cuff 102 and foot bed 104 are pivotally connected, such as by a hinge mechanism. Pivot points are preferably provided along both the medial and lateral sides of the foot bed 104, with the lateral pivot 106 being slightly lower than the medial pivot 108. This arrangement of the pivots 106, 108 enables the pivoting action of the ankle cuff 102 with respect to the foot bed 104 to match the natural pivoting motion of the wearer's ankle in dorsi-flexion and plantar-flexion. The ankle cuff 102 and foot bed 104 are preferably sufficiently flexible for conforming to the shape of the wearer's foot, ankle, and lower leg, while being sufficiently rigid to protect against injury. If desired, the foot bed 104 may be heat-formed or otherwise molded to conform to the wearer's foot for additional comfort. When assembled, the semi-rigid shell 101 is preferably open toed and open heeled.

Figure 7:
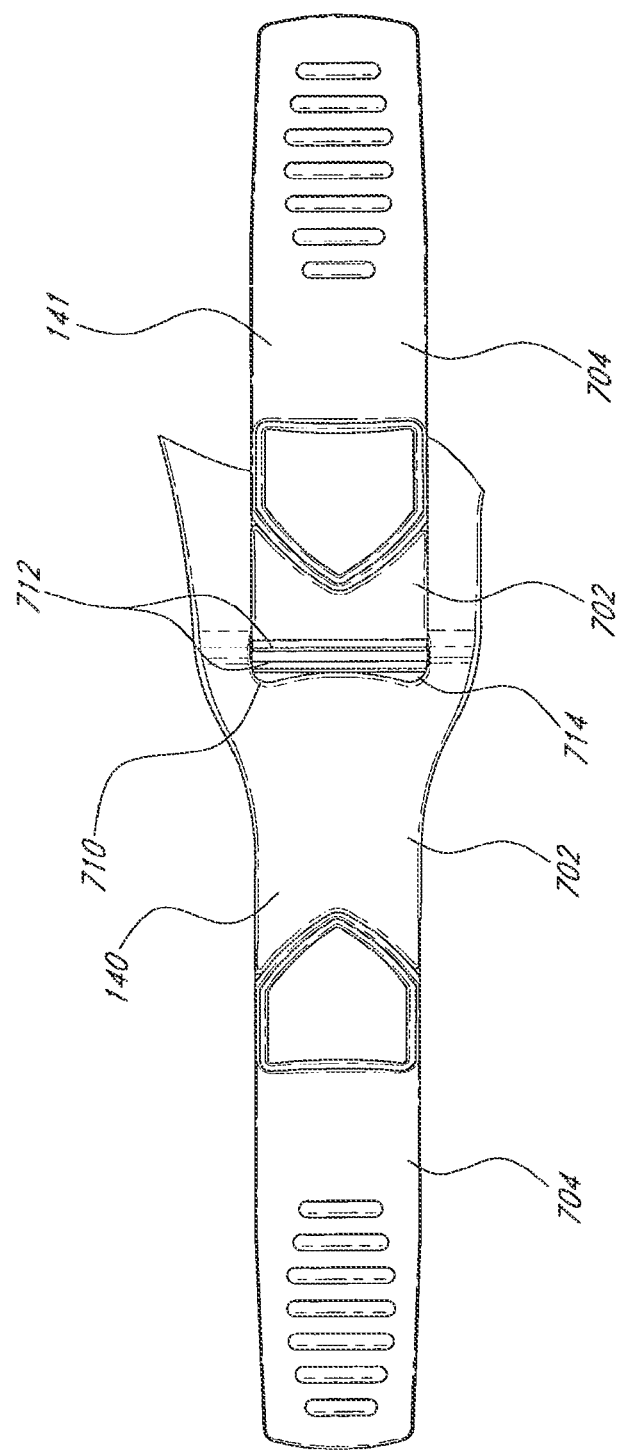
FIG. 7 is a detail front elevational view of the curved slot and ratchet mechanism of the semi-rigid straps of the ankle brace of FIG. 1.
Figure 8:
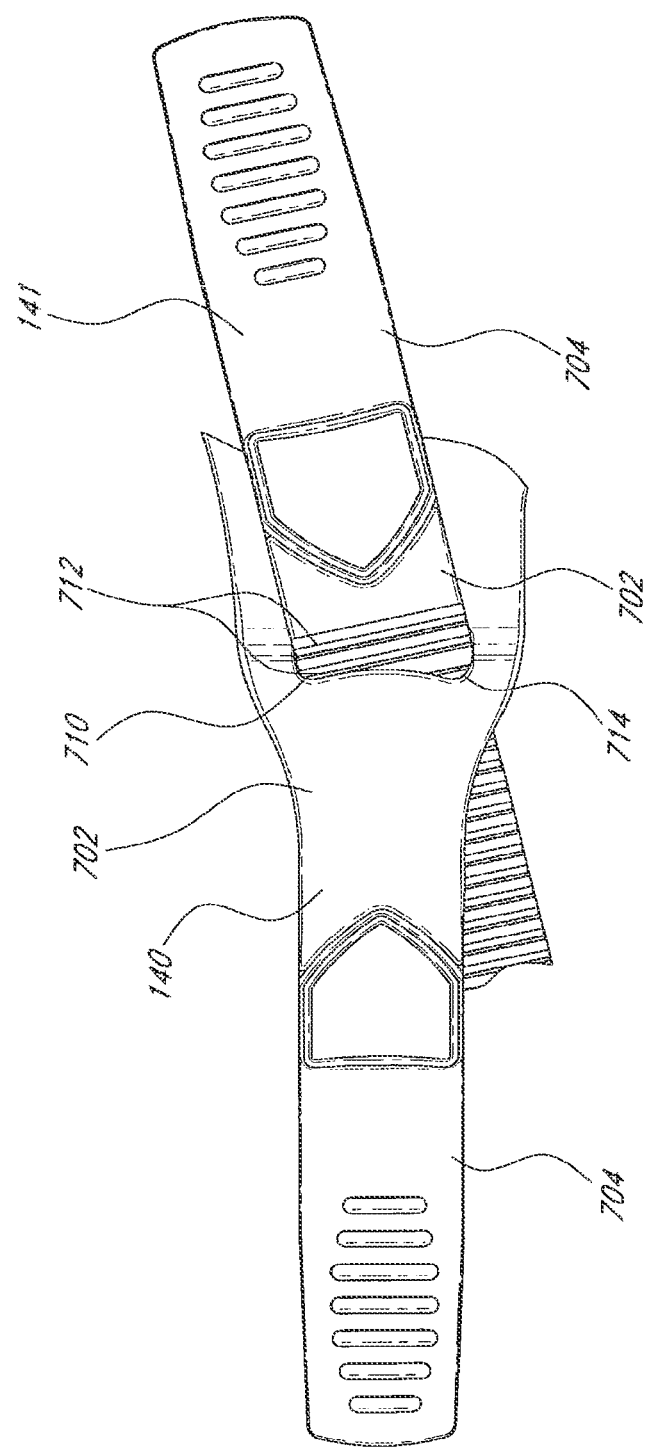
FIG. 8 is a detail front elevational view of the curved slot and ratchet mechanism of FIG. 7 in a first rotated position.
Figure 9:
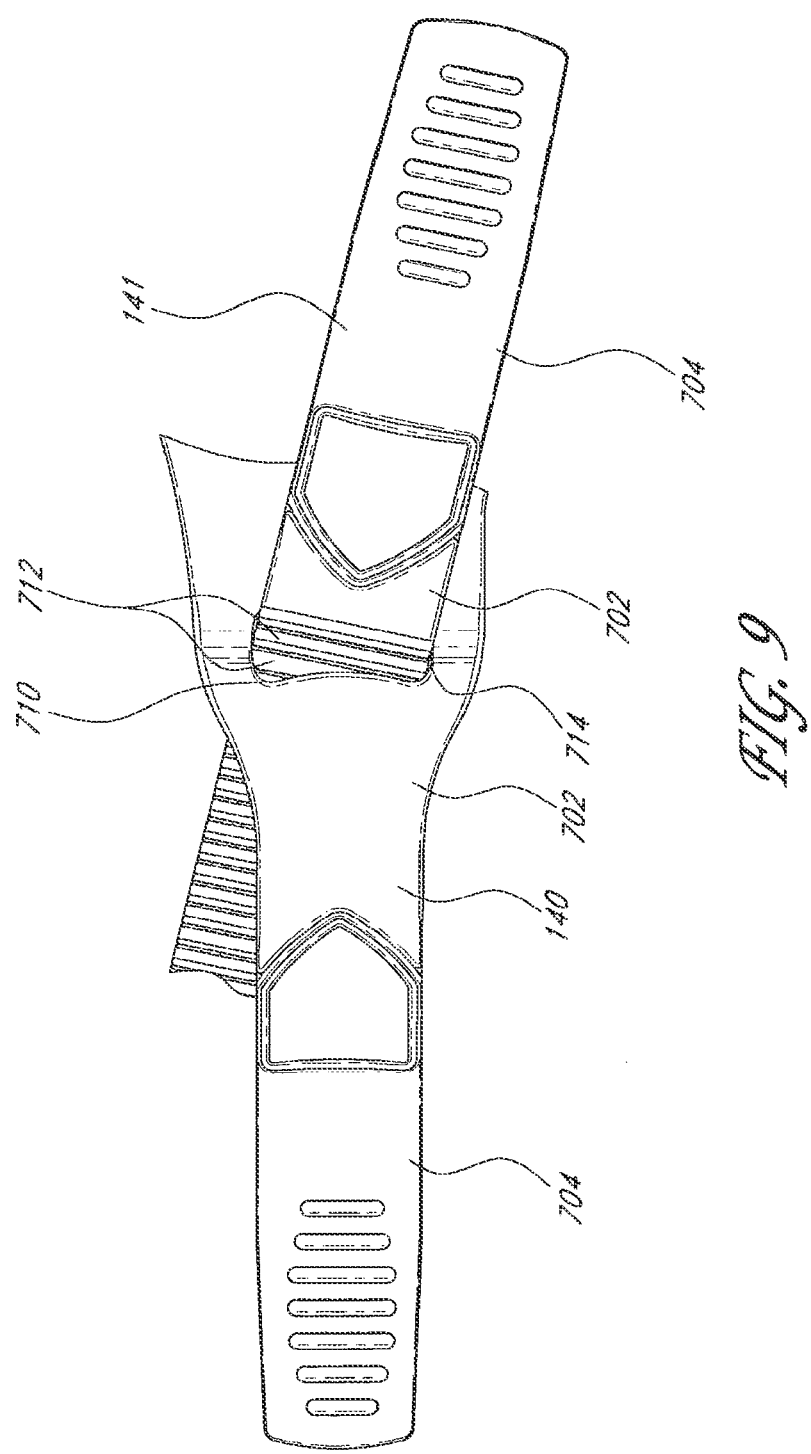
FIG. 9 is a detail front elevational view of the curved slot and ratchet mechanism of FIG. 7 in a second rotated position.
Figure 10:
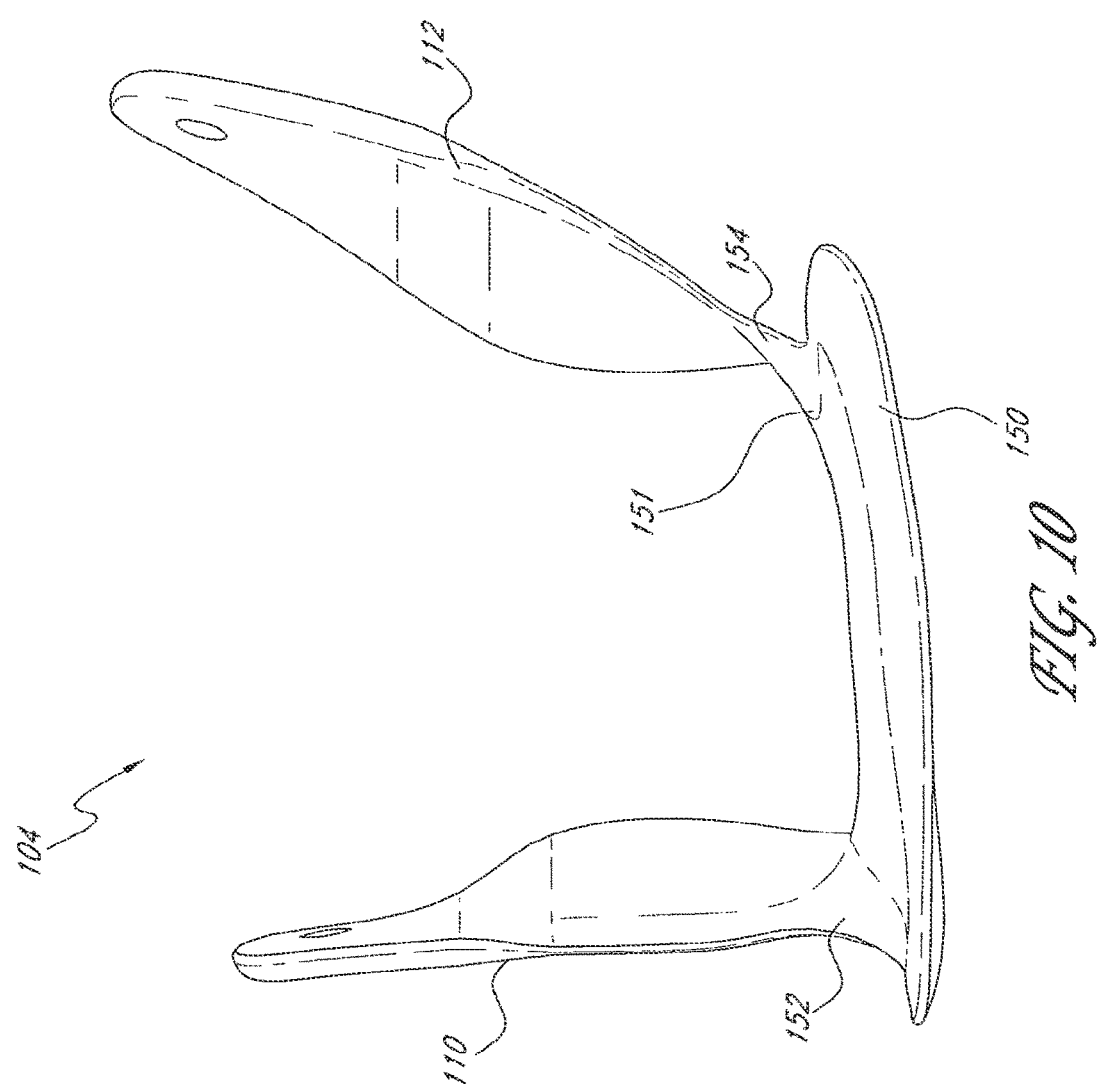
FIG. 10 is a front elevational view of the foot bed of the hinged ankle brace of FIG. 1.

With reference to FIGS. 2 and 7, in the illustrated embodiment, a medial strap 140 and a lateral strap 141 extend forward from the ankle cuff 102. The straps 140, 141 are preferably semi-rigid and include a ratchet mechanism to incrementally tighten the cuff and maintain the desired tension. The lateral strap 141 preferably extends through a slot 710 in the medial strap 140 having a curved shape 714 for allowing the straps 140-141 to angularly adjust. As best illustrated in FIGS. 7-9, this feature accommodates medial/lateral cuff flexing for additional comfort and effectiveness during use. It will further be appreciated by those skilled in the art that the interlocking nature of the strap provides excellent torsional rigidity and improved eversion and inversion control.

Upper Ankle Cuff

Figure 4:
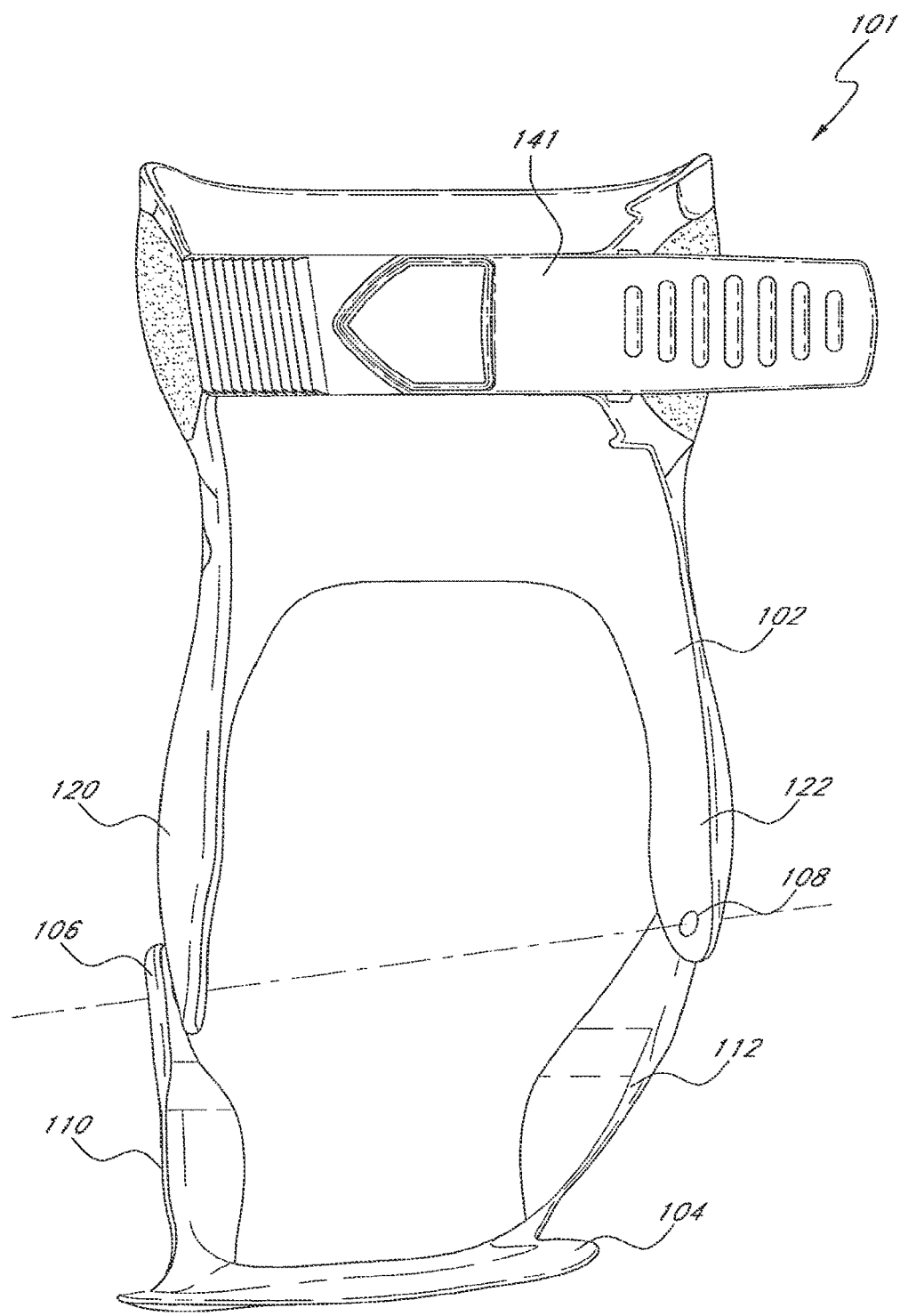
FIG. 4 is a front elevational view of the semi-rigid shell of FIG. 2.

With reference to FIGS. 1 and 2, the upper ankle cuff 102 includes a calf-supporting portion 121 shaped and configured to support a posterior side of the wearer's calf. A lateral upright 120 extends downward from a lateral side of the calf-supporting portion 121, and a medial upright 122 extends downward from a medial side of the calf-supporting portion 121. A lower end of the lateral upright 120 is pivotally attached to a corresponding lateral wing 110 extending upward from a lateral side of the foot bed 104 with a lateral hinge 106. A lower end of the medial upright 122 is pivotally attached to a corresponding medial wing 112 extending upward from a medial side of the foot bed 104 with a medial hinge 108. These pivotal attachments 106, 108 allow the upper ankle cuff 102 and the foot bed 104 to pivot with respect to each other such that the ankle brace allows the ankle of a wearer to flex in dorsi-flexion and plantar-flexion. With reference to FIG. 4, in certain embodiments, the pivots 106, 108 may be arranged such that the medial pivot 108 is higher with respect to the foot bed 104 than the lateral pivot 106. Thus, the centers of the axes of rotation for each pivot 106, 108 are offset from one another, as illustrated in FIG. 4. Additionally, the axes of rotation are skewed relative to a horizontal plane. Advantageously, this offset and skewed geometry of the pivots 106, 108 closely resembles the anatomy of a human ankle, thus allowing the brace to closely simulate the natural bending motion of the human ankle.

In certain embodiments, the upper ankle cuff 102 may be comprised of a heat moldable material. For example, certain polyamide and polyamide/ABS composite materials may have the desired heat moldability. In these embodiments, advantageously, the upper ankle cuff 102 may be individually molded to accurately conform to the particular calf anatomy of a wearer. A heat gun or other readily available heating device may be used to raise the temperature of the upper ankle cuff 102 so that it becomes moldable, allowing each individual wearer to create a custom-fit ankle cuff 102.

Semi-Rigid Straps

With continued reference to FIGS. 1 and 2, in certain embodiments the ankle brace 100 includes a semi-rigid medial strap 140 and a semi-rigid lateral strap 141. The semi rigid straps 140, 141 are configured to adjustably position the ankle cuff 102 on the ankle of a wearer. In the illustrated embodiments, at least a portion of each semi-rigid strap 140, 141 is formed integrally with the upper ankle cuff 102. For example, these portions could be molded as one piece of polyamide or a composite of polyamide and ABS. The medial strap 140 extends forward from a medial side of the upper ankle cuff 102, and the lateral strap 141 extends forward from a lateral side of the upper ankle cuff 102. FIG. 1 illustrates the straps 140, 141 in an engaged position, and FIG. 2 illustrates the straps in a disengaged position.

As depicted in FIGS. 7-9, the ratcheted adjustment of the medial strap 140 with respect to the lateral strap 141 is provided by the engagement between a slot 710 disposed on the medial strap 140 and a plurality of ridges 712 disposed on the lateral strap 141. However, it is recognized that other ratchet mechanisms known in the art could be incorporated into the straps 140, 141 of the ankle brace. A curved edge 714 of the slot 710 engages one of the plurality of ridges 712, thus maintaining the position of the two straps relative to each other. Advantageously, the ratcheted interconnection allows a wearer to repeatedly and reliably adjust the straps to a desired size of the ankle brace. The wearer may note the number of ridges 712 advanced through the slot 710 when the ankle brace 100 is properly sized. By advancing the same number of ridges 712 through the slot 710 during each fitting, the wearer is able to repeatedly and consistently achieve the same incremental adjustment of the ankle brace.

With reference to FIGS. 7-9, in the illustrated embodiments the engagement side of the slot 710 includes a curved profile 714. This curved profile 714 allows ratcheted interconnection of the two straps 140, 141 even over a range of angles where the straps 140, 141 are transverse to each other. FIGS. 8 and 9 illustrate the ratcheted interconnection of the straps 140, 141 over a range of transverse orientations of the straps 140, 141 relative to each other. In FIG. 8, the straps are in a first rotated position. In FIG. 9, the straps are in a second rotated position relative to each other. The curved profile 714 of the slot 710 allows the slot 710 to maintain contact with the ridges 712 for all rotated positions in a range between the first rotated position and the second rotated position. Advantageously, this contact between the slot 710 and the ridges 712 allows the straps 140, 141 to securely conform to any of various ankle sizes and geometries. Additionally, the curved profile 714 maintains the ratcheted interconnection between the straps 140, 141 even where a wearer's walking or running motion rotates the straps relative to each other.

With reference to FIGS. 5-9, each of the straps 140, 141 may comprise of a first segment 702 adjacent the ankle cuff 102 and a second segment 704 spaced from the ankle cuff 102. These segments 702, 704 may comprise materials having different rigidities. In one embodiment, the first segment 702 is semi-rigid, and, as noted above, is formed as a single, unitary piece with the upper ankle cuff 102. The second segment 704, however, may be relatively less rigid. Therefore, the increased flexibility of the second segment 704 advantageously allows the straps 140, 141 to closely conform to the shape of the outer surface of the ankle cuff 102, thus tightly conforming the ankle brace to a wearer's ankle. The semi-rigid first segment 702 contributes to the overall support and stability provided to a wearer's ankle by the ankle brace 100. The first segments 702 of the ratchetably interconnecting straps 140, 141, combined with the calf-supporting portion 121 (FIG. 1), completely encircle the wearer's ankle. Advantageously, since the ankle brace 100 provides a semi-rigid structure completely encircling the ankle of the wearer, it provides enhanced resistance to high ankle sprains as compared to an ankle brace including only a soft strap.

The second segments 704 may be configured to mate with outer surfaces of the ankle cuff 102 through the use of fasteners such as, for example, hook-and-loop fasteners. In a preferred embodiment, as illustrated in FIG. 2, each second segment 704 includes a patch of hook fasteners 204 disposed on an inner surface. An outer surface of the calf-supporting portion 121 includes a patch of loop fasteners 202 disposed thereon. When the strap 140 is in an engaged position (FIG. 1), the hook fasteners 204 and loop fasteners 202 mate to secure the straps 140, 141. Those of skill in the art will appreciate that the locations of the hook fasteners and the loop fasteners could be switched to position the loop fasteners on the straps 140, 141 and the hook fasteners on the ankle cuff 102. Those of skill in the art will further appreciate that other fasteners such as snaps, buttons, laces, zippers, or other similar fasteners could be used to adjustably secure the second segments 704 to the ankle cuff 102.

Foot Bed

With reference to FIGS. 1-3 and 10, the foot bed 104 includes a contoured lower foot plate 150, a lateral wing 110, and a medial wing 112. The wings 110, 112 extend generally upwardly from medial and lateral edges, respectively, of a posterior portion of the foot plate 150. The contours of the foot plate 150 preferably follow the natural contours of the sole of a typical human foot. For example, the foot plate 150 includes a raised portion 151 that mates with the concavity of the wearer's arch. The foot plate 150 underlies the entire width of the wearer's foot and extends from adjacent the ball of the wearer's foot to adjacent the wearer's heel. Therefore, the foot plate 150 provides a relatively large coverage area and sole-conforming contours that reduce the incidence of foot slippage from the foot plate 150. This large coverage area provides various advantages over a stirrup-like foot retaining section as has been previously disclosed. For example, U.S. Pat. Nos. 6,524,266 and 6,656,145 disclose stirrup-like foot retaining portions. In contrast to these stirrup-like foot retaining sections, which rely on only a narrow strip of material contacting a wearer's foot for all support of that foot, the foot plate 150 of the illustrated embodiments provides a larger contact area between the wearer's foot and the foot plate 150. This larger contact area contributes to greater control against inversion, eversion, and rotation of a wearer's foot, at least in part by reducing the risk of foot slippage with respect to the foot plate 150. Further, the sole-conforming contours of the foot plate 150 also reduce the incidence of foot slippage from the foot plate 150, which provides further control against inversion, eversion, and rotation of the wearer's foot.

Figure 5:
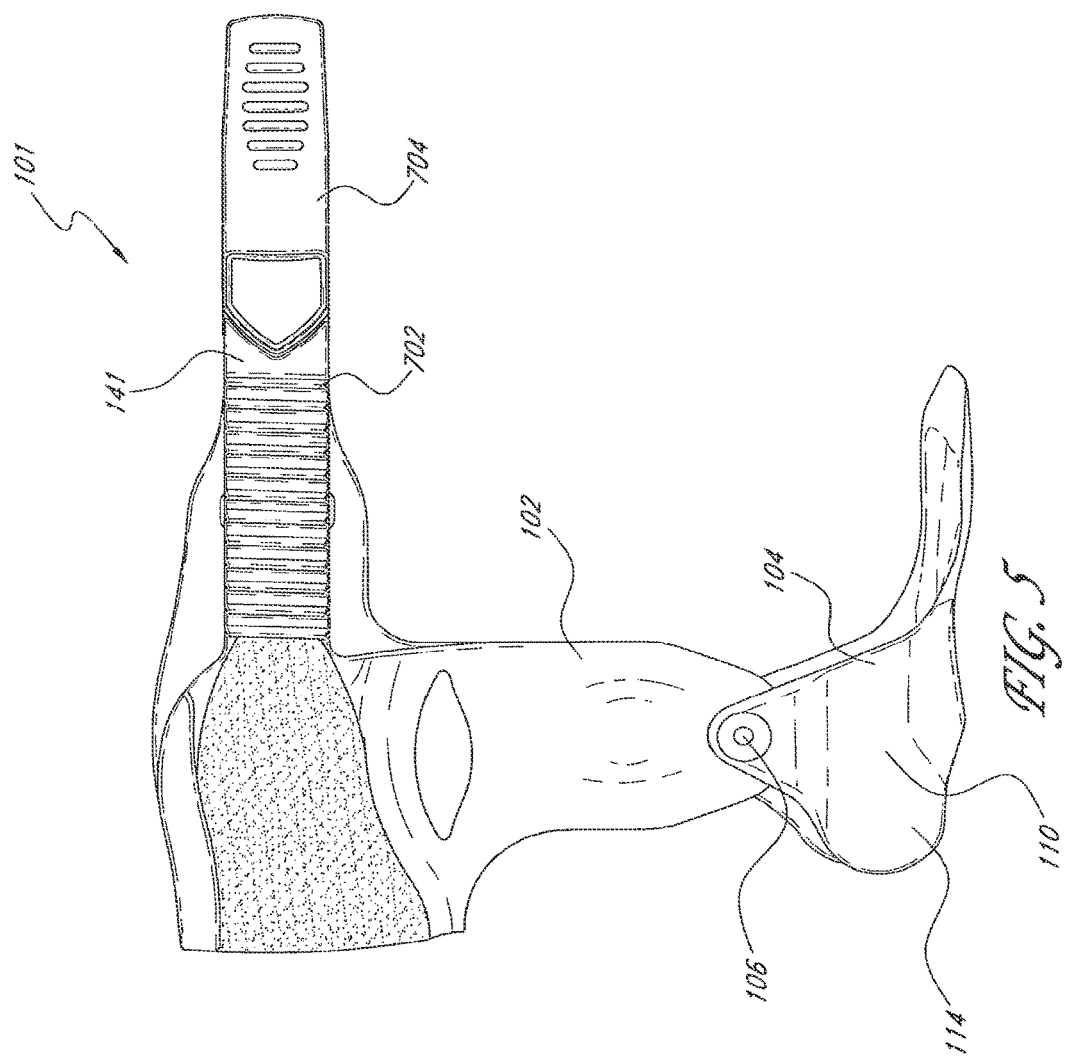
FIG. 5 is a left-side elevational view of the semi-rigid shell FIG. 2.
Figure 6:
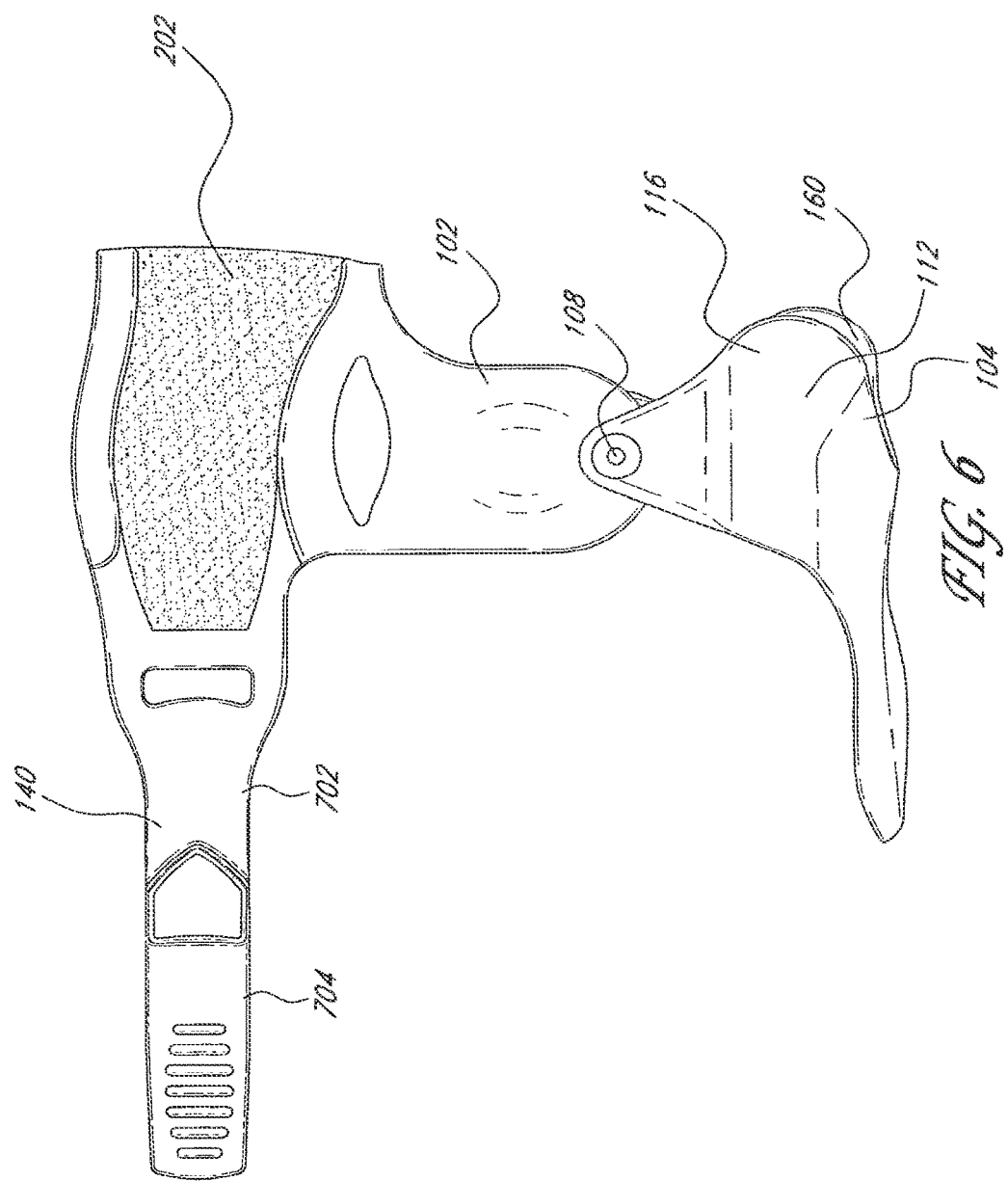
FIG. 6 is a right-side elevational view of the semi-rigid shell FIG. 2.

With references to FIGS. 5 and 6, which depict left and right side views of the semi-rigid shell 101, the lateral wing 110 includes a lateral posterior extension 114, and the medial wing 112 includes a medial posterior extension 116. Each of the posterior extensions 114, 116 is shaped substantially as a rounded lobe in side elevational view, and each is configured to cup and support each side of the wearer's ankle and heel. The posterior extensions 114, 116 thus provide calcaneal support to the wearer and prevent unnatural inversion and eversion.

The lateral and medial wings 110, 112 may be connected to the foot plate 150 by a medial bend region 152 and a lateral bend region 154 (FIG. 10) interposed between the foot plate 150 and corresponding lateral and medial wings 110, 112. These bend regions 152, 154 may be slightly more flexible than the foot plate 150 to facilitate conformance of the ankle brace with the anatomy of a particular wearer. For example, the bend regions 152, 154 may be formed of the same material as the foot plate 150, but be less thick than the foot plate 150. The bend regions 152, 154 advantageously allow the ankle brace to fit a given individual well despite variations in anatomical geometry across the general population.

The lateral and medial wings 110, 112 are configured to be pivotally coupled to the lateral and medial uprights 120, 122 of the upper ankle cuff 102. With reference to FIG. 2, a medial hinge 108 pivotally couples the medial wing 112 of the foot bed 104 with the medial upright 122 of the ankle cuff 102 and a lateral hinge 106 pivotally couples the lateral wing 110 of the foot bed 104 with the lateral upright 120 of the ankle cuff 102. As discussed above, in certain embodiments, the medial pivot 108 is higher with respect to the foot plate 150 than the lateral pivot 106. Advantageously, this geometry closely resembles the anatomy of a human ankle, thus allowing the ankle brace to closely simulate an ankle's natural bending motion. As depicted, the lateral and medial hinges 106, 108 comprise rotatable riveted connections. However, those of skill in the art will appreciate that other rotatable connections could be used instead.

Figure 3:
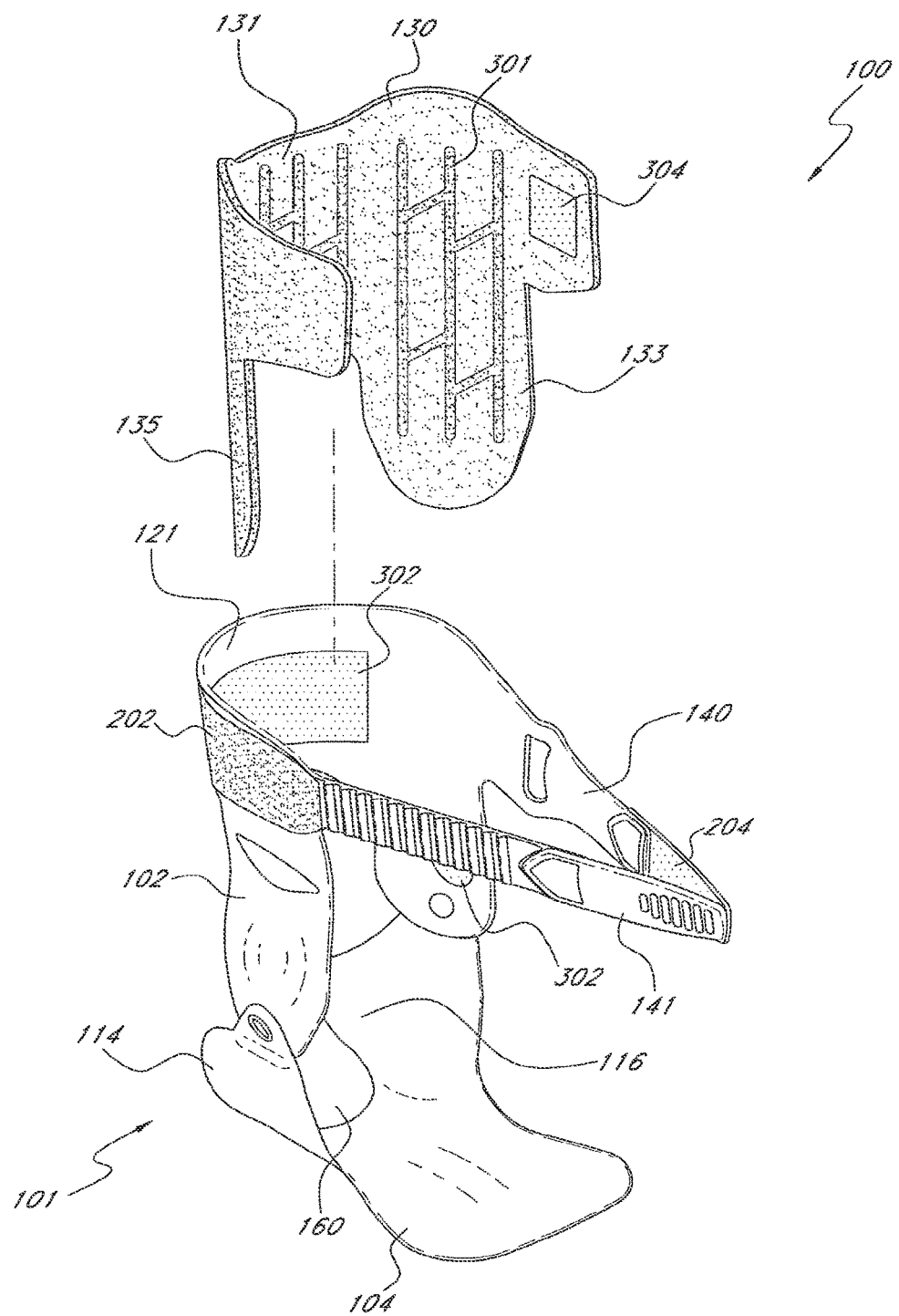
FIG. 3 is a partially exploded front perspective view of the hinged ankle brace of FIG. 1, illustrating an inner liner of the brace removed from the semi-rigid shell.

With reference to FIGS. 1-3, a substantially semi-circular cut-out portion 160 of the foot plate 150 receives the wearer's heel. As explained above, in certain embodiments, the ankle brace 100 may be worn within a shoe of a wearer. The cut-out portion 160 enables the wearer's heel to engage the insole of the wearer's shoe, such that the foot plate 150 does not interfere with the cushioning provided by the shoe. Likewise, in the illustrated embodiments the foot bed 104 does not extend under the ball of the wearer's foot, thus allowing the shoe to cushion standing, walking, and running loads on the heel and the ball of the wearer's foot.

In certain embodiments, the foot bed 104 may be comprised of a heat moldable material. For example, certain polyamide and polyamide/ABS composite materials may have the desired heat moldability. In these embodiments, advantageously, the foot bed 104 may be individually molded to accurately conform to the particular foot anatomy of a wearer or a particular shoe or orthotic to be worn by the wearer. A heat gun or other readily available heating device may be used to raise the temperature of the foot bed 104 so that it becomes moldable, allowing each individual wearer to create a custom-fit foot bed 104.

In certain embodiments, the foot bed 104 may be comprised of a trimmable material. For example, certain polyamide and polyamide/ABS composite materials may be trimmable. In these embodiments, advantageously, material may be trimmed from the foot bed 104 to accurately conform the foot bed 104 to the foot anatomy of a particular wearer or to a shoe of the wearer. Scissors, knives, saws, rotary tools, or other cutting devices may be used to trim the foot bed 104.

Inner Liner

In certain embodiments, the present ankle brace includes an inner liner. As depicted in FIGS. 1, 3 and 11-12, the inner liner 130 is sized and shaped to underlie the ankle cuff 102. With reference to FIG. 3, the inner liner 130 has a calf-supporting portion 131 configured to encircle the wearer's lower calf, a medial upright 133 extending downward from a medial side of the calf-supporting portion, and a lateral upright 135 extending downward from the lateral side of the calf-supporting portion. FIG. 3 illustrates a partially exploded view of the ankle brace 100 with its inner liner 130 removed from its semi-rigid shell 101. The inner liner 130 may be comprised of a soft, compressible material. In one embodiment, the inner liner 130 is comprised of an EVA foam inner cushion in a brushed polyamide outer layer. Alternatively, the inner liner 130 could be comprised of polyurethane foam, polyethylene foam, microspheres (such as glass) contained in a lubricant matrix (such as mineral oil), other gels and foams, or pneumatics. Advantageously, the inner liner 130 provides a comfortable fit for the wearer as well as stability.

The inner liner 130 may include at least one generally vertical channel 301. The channel 301 is formed on an inner surface of the inner liner 130. The channel may extend below the surface of the inner liner 130. The channel 301 allows the inner liner 130 to flex. This flexibility enhances the ability of the inner liner 130 to encircle and maintain contact with ankles having a variety of sizes and shapes.

The inner liner 130 is preferably removable from the ankle cuff 102. FIG. 1 illustrates the ankle brace 100 with an inner liner 130 inserted in the ankle cuff 102. FIGS. 2-6 illustrate a semi-rigid shell 101 of the ankle brace 100 with the inner liner 130 removed. Preferably, this removability may be achieved with hook-and-loop fasteners. In certain embodiments, a portion of a brushed polyamide surface of the inner liner 130 serves as the loop component of a hook-and-loop fastener. At least one patch of hooks 302 (FIGS. 2, 3) may be adhered to an inner surface of the ankle cuff 102 such that the inner liner 130 may be removably attached thereto. Alternatively, other fasteners known in the art such as snaps, zippers, buttons, or adhesive strips may be used to removably or permanently attach the inner liner 130 to the ankle cuff 102. Advantageously, a removable inner liner 130 may be removed for various reasons including to be cleaned, dried, laundered, or replaced with an inner liner 130 of a different size.

With reference to FIG. 3, the calf-supporting portion 131 of the inner liner 130 is shaped and configured to provide support for the posterior of the wearer's ankle and is open at an anterior side to allow the wearer to easily don the inner liner 130. The inner liner 130 may also comprise an adjustable fastener such that the inner liner 130 may be adjustably conformed to a wearer's ankle. Preferably, this adjustable fastener comprises a hook-and-loop fastener. The outer surface of the inner liner may serve as a loop portion of a hook-and-loop fastener, configured to mate with a patch of hooks 304 on an inner surface of the inner liner 130. Other fasteners such as laces, snaps, buttons, zippers or other similar adjustable fasteners may be used to adjust the inner liner 130.

Figure 14:
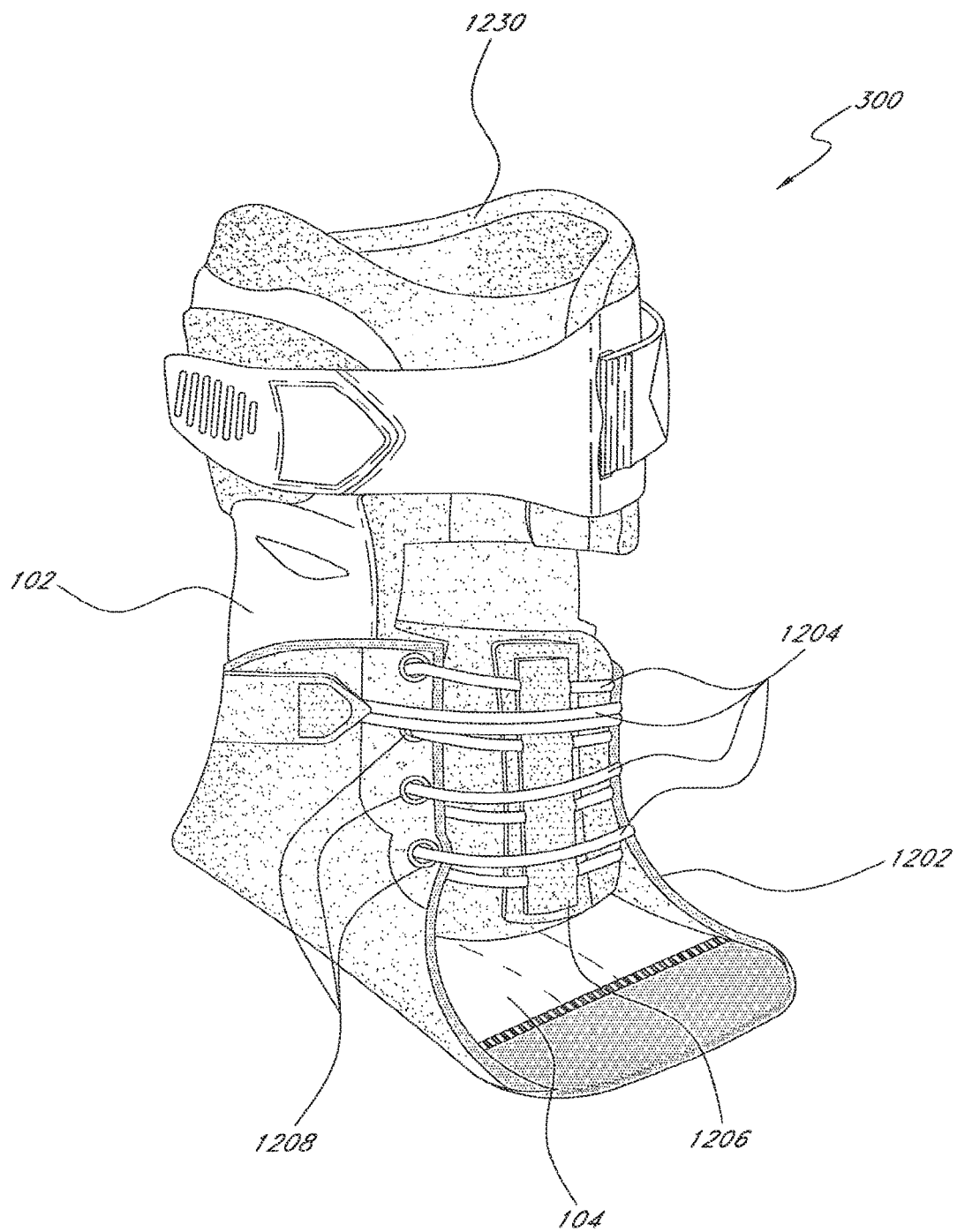
FIG. 14 is a front perspective view of another preferred embodiment of the present hinged ankle brace.

FIGS. 14-16 illustrate another embodiment of the present ankle brace 300 in which an inner liner 1230 additionally includes an Achilles heel pad 1234 to provide enhanced comfort and stability to a wearer's ankle. FIG. 16 illustrates the inner liner 1230 to be used with the ankle brace 300 in the embodiment illustrated in FIG. 14. The inner liner 1230 includes a calf-supporting portion 1221 sized and configured to encircle the wearer's lower calf, a lateral upright 1220 extending downward from a lateral side of the calf-supporting portion, a medial upright 1222 extending downward from a medial side of the calf-supporting portion, and an Achilles heel pad 1234 extending downward from a posterior side of the calf-supporting portion 1221. The medial and lateral uprights 1220, 1222 extend anteriorly such that they overlap at an anterior face of the inner liner 1230. The Achilles heel pad 1234 provides additional comfort and support to the wearer's heel. Additionally, the Achilles heel pad provides cushioning to the wearer's heel when the inner liner 1230 is worn in conjunction with a compressive outer sleeve 1202 as depicted in FIG. 15 and discussed further below. Preferably, the Achilles heel pad 1234 has at least one vent 1232 therein to promote breathability of the ankle brace.

Outer Sleeve

Figure 11:
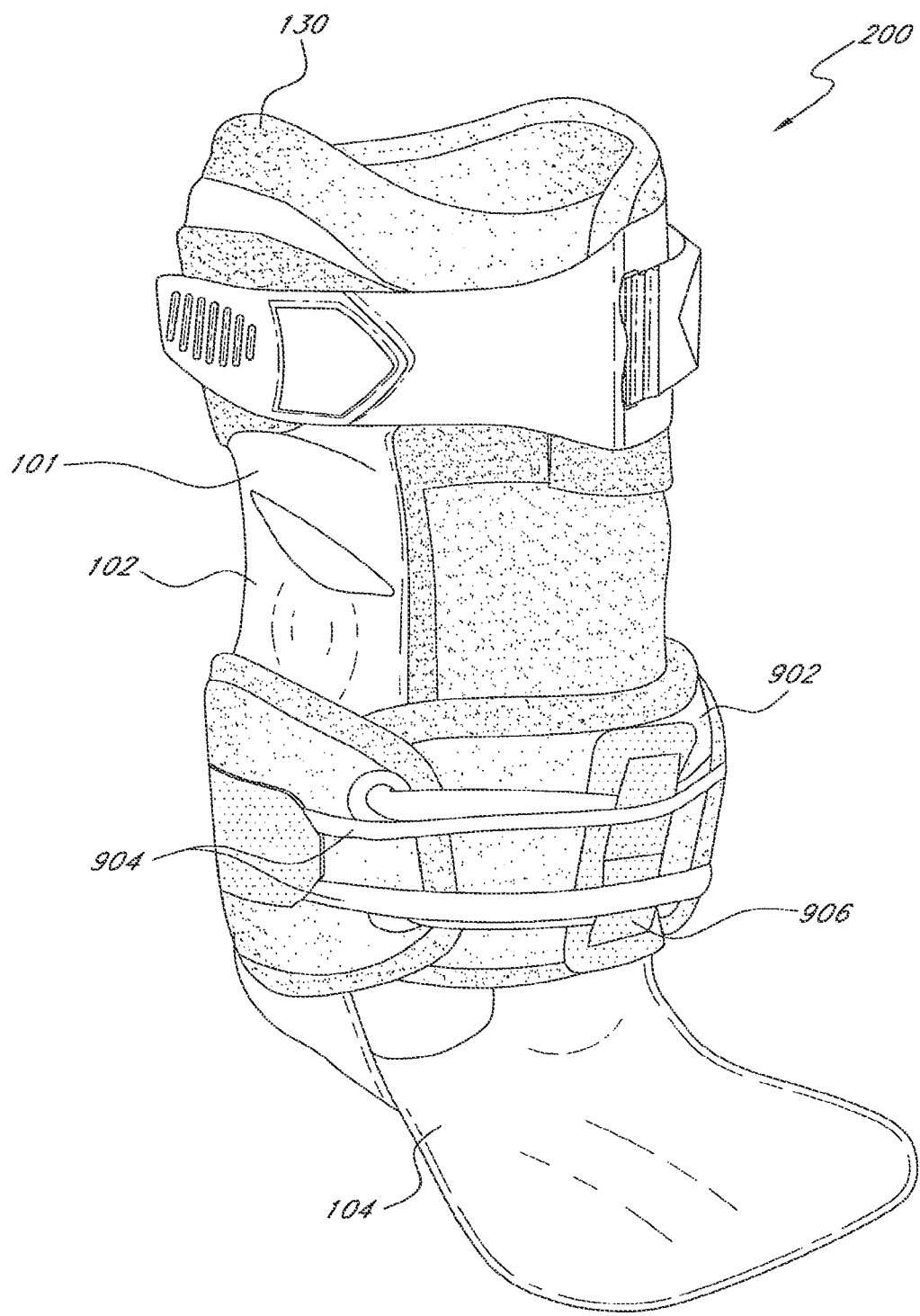
FIG. 11 is a front perspective view of another preferred embodiment of the present hinged ankle brace.
Figure 12:
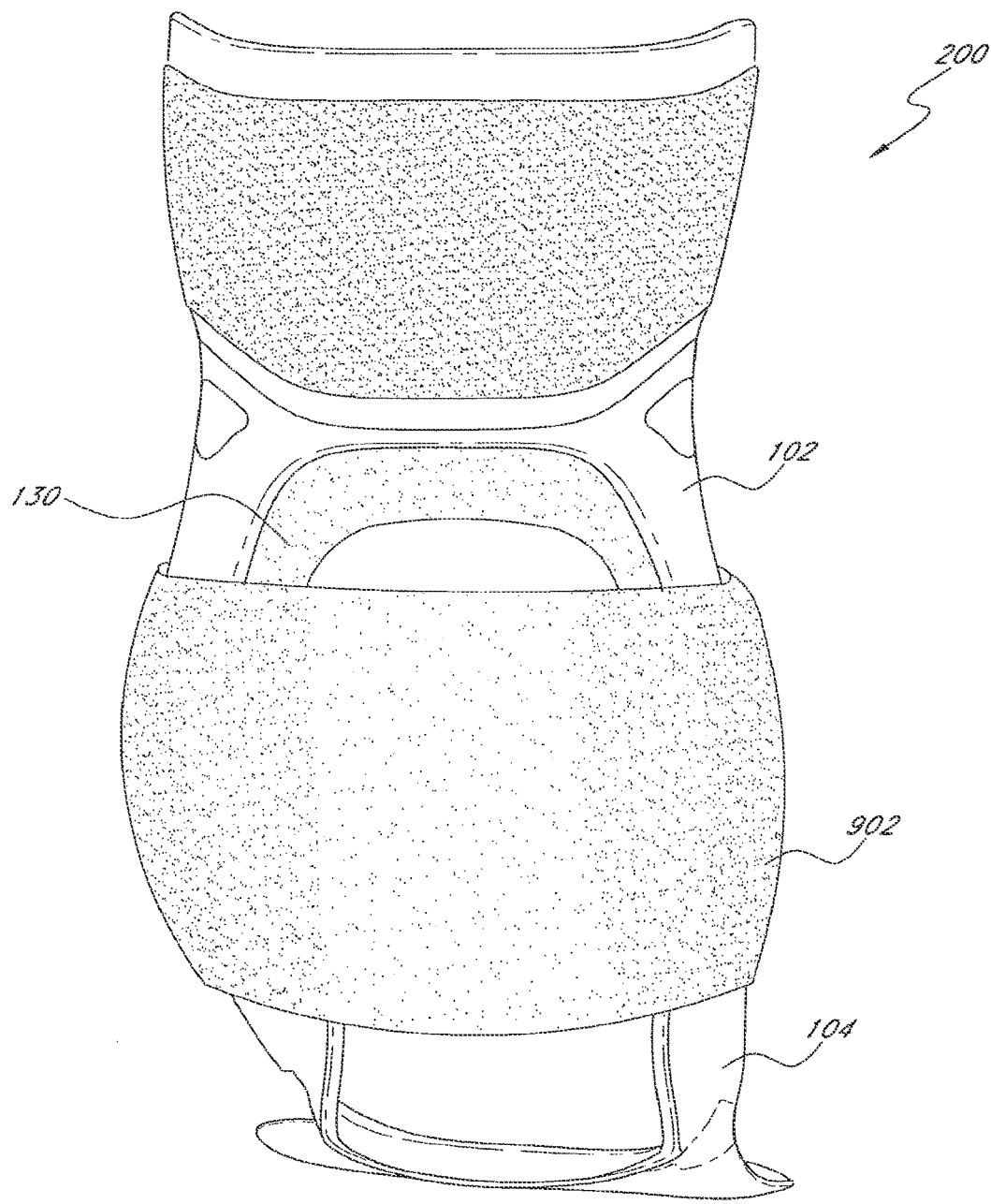
FIG. 12 is a rear elevational view of the hinged ankle brace of FIG. 11.

FIGS. 11 and 12 illustrate another embodiment of the present ankle brace 200, which comprises a removable outer sleeve 902. The outer sleeve 902 is an adjustable soft band that is sized and configured to encircle the semi-rigid shell 101 at a location overlying the wearer's ankle joint. In the illustrated embodiments, the outer sleeve 902 is a generally rectangular band whose ends may be overlapped to form a generally cylindrical segment whose inner diameter can be varied by adjusting the amount of overlap of the ends.

Figure 13:
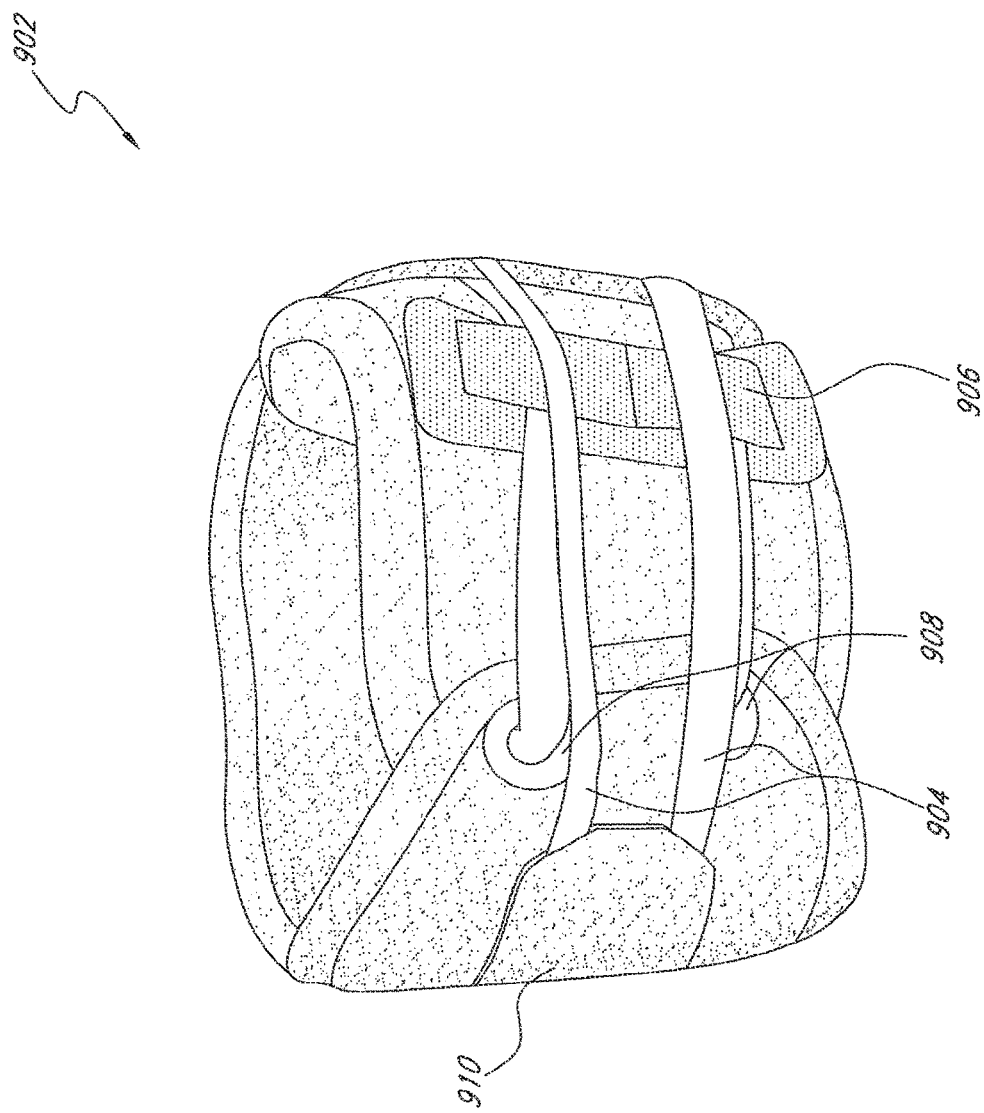
FIG. 13 is a front perspective view of an outer sleeve of the hinged ankle brace of FIG. 11.

The outer sleeve is best illustrated in FIG. 13. The outer sleeve 902 may be comprised of a relatively inelastic fabric that is strong and durable such as a polyester material. The outer sleeve 902 is configured to be positioned outside the ankle cuff 102 at a location approximately overlying the ankle joint of a wearer. The outer sleeve 902 thus provides ankle joint compression to a wearer by compressing the semi-rigid ankle cuff 102 and foot bed 104 around the ankle of a wearer. This ankle joint compression provides additional support to the wearer's ankle joint.

The circumference of the outer sleeve 902 is preferably securably adjustable. As depicted this securable adjustability is provided by a plurality of laces 904 passing through a tongue lace guide 906 and opposing eyelets 908 on the outer sleeve 902. Ends of the laces 904 are securable to the outer sleeve 902 with hook-and-loop fasteners 910. In the illustrated embodiments, the outer surface of the outer sleeve 902 forms the loop portion of the fastener, and the hook portion is provided by a patch to which the ends of the laces are affixed. Advantageously, this combination of laces 904 with hook-and-loop fasteners 910 facilitates rapid application, adjustment, and removal of the outer sleeve 902. But, it is recognized that other fastening devices such as knotted laces, flexible hook-and-loop straps, elastic bands, and other similar securable adjustable devices may be used in conjunction with an outer sleeve 902 to provide the desired ankle joint compression.

In other embodiments, as depicted in FIGS. 14-16, an ankle brace 300 may further comprise a removable outer sleeve 1202 that provides enhanced support. The outer sleeve 1202 is configured to overlie the foot bed 104 and a lower portion of the ankle cuff 102. The outer sleeve 1202 thus provides enhanced support to a wearer by compressing the foot bed 104 around the wearer's foot and by compressing ankle cuff 102 around the wearer's ankle joint. The outer sleeve 1202 is preferably adjustably securable. A plurality of laces 1204 interwoven through a tongue lace guide 1206 and opposing eyelets 1208 on the outer sleeve 1202 may provide this adjustable securability. Ends of the laces 1204 may be adjustably secured to the outer sleeve 1202 with hook-and-loop fasteners substantially as described above with respect to the embodiments of FIGS. 11-13. Also, other suitable fasteners such as knotted laces, flexible hook-and-loop straps, elastic bands, or other similar securable adjustable devices may be used in conjunction with an outer sleeve providing enhanced support.

Applying the Present Ankle Brace

A wearer may don the ankle brace illustrated in FIGS. 1-10 with the semi rigid shell 101 and the inner liner 130 in an open configuration as illustrated in FIG. 3. The wearer applies the inner liner 130 to his or her lower calf such that the calf-supporting portion 131 covers a posterior side of the wearer's ankle and the lateral and medial uprights 135, 133 extend down corresponding lateral and medial sides of the wearer's ankle. The wearer may then secure the inner liner 130 around the ankle by applying the patch of hooks 304 to a loop portion formed on a surface of the inner liner 130. The wearer also securably positions the inner liner 130 in the semi-rigid shell 101 such that the inner liner 130 is substantially aligned with the ankle cuff 102. Patches of hooks 302 may mate with an outer surface of the inner liner 130 to secure the inner liner 130 with respect to the semi-rigid shell 101. The inner liner 130 may be securely positioned in the semi rigid shell 101 before the wearer applies the inner liner to the ankle. Alternatively, the inner liner 130 and semi-rigid shell 101 may be applied in sequence. As the wearer applies the inner liner 130 and securely positions the inner liner 130 in the semi-rigid shell 101, the wearer's foot should align with the foot bed 104 such that the wearer's heel is in the cut-out portion 160 of the foot bed 104, the sole of the wearer's foot is resting on the foot bed 104, and the ball of the wearer's foot is adjacent the foot bed 104.

The wearer then interconnects the straps 140,141 by passing an end of the lateral strap 141 through the slot 710 of the medial strap 140. As discussed above, the wearer may incrementally adjust the straps 140,141 by advancing a desired number of ridges 712 on the lateral strap 141 through the slot 710. Once a desired adjustment has been achieved, the wearer secures ends of the straps 140, 141 to the ankle cuff 102. This securing may be accomplished by fastening hook fasteners 204 on the second segments 704 of the straps 140, 141 to loop portions 202 on a surface of the ankle cuff 102.

To don other embodiments of ankle brace as illustrated in FIGS. 11-15, the wearer may also apply an outer sleeve 902 (FIGS. 11-13), 1202 (FIGS. 14-15). In certain instances, the outer sleeve 902, 1202 may have been previously applied to the semi-rigid shell 101 such that to apply the outer sleeve 902, 1202 the wearer inserts a foot through the outer sleeve 902, 1202 and advances the foot and ankle until the ankle brace 200, 300 is appropriately positioned around the wearer's foot and ankle as discussed above. The wearer would then securably adjust the outer sleeve 902, 1202, by tightening laces on the outer sleeve 902, 1202 and securing the ends of the laces by, for example, using a hook and loop fastener. Alternatively, the wearer may apply the outer sleeve 902, 1202, after the semi-rigid shell 101 has been applied. The wearer would slidably advance the outer sleeve 902, 1202 over the foot in the foot bed 104 of the semi-rigid shell 101, into the appropriate position. In applying a band type outer sleeve of the embodiments illustrated in FIGS. 11-13, the outer sleeve 902 would be advanced until it overlies the wearer's ankle. In applying an outer sleeve with enhanced support, as illustrated in FIGS. 14-15, the outer sleeve 1202 would be advanced until it substantially covers a lower surface of the foot plate 104. Once advanced, the outer sleeve 902, 1202 would be securely adjusted using an adjustable fastener at the end of the laces.

Scope of the Invention

The above presents a description of the best mode contemplated for carrying out the present ankle brace, and of the manner and process of making and using it, in such full, clear, concise, and exact terms as to enable any person skilled in the art to which it pertains to make and use this ankle brace. This ankle brace is, however, susceptible to modifications and alternate constructions from that discussed above that are fully equivalent. Consequently, this ankle brace is not limited to the particular embodiments disclosed. On the contrary, this ankle brace covers all modifications and alternate constructions coming within the spirit and scope of the ankle brace as generally expressed by the following claims, which particularly point out and distinctly claim the subject matter of the ankle brace.

What is claimed is:

1. An ankle brace comprising:
a semi-rigid ankle cuff including a calf-supporting portion configured to extend around a posterior side of a lower calf of a wearer, a medial upright extending generally downward from a medial side of the calf-supporting portion, and a lateral upright extending generally downward from a lateral side of the calf supporting portion, wherein said semi-rigid ankle cuff is moldable to custom fit a wearer of said ankle brace;
a semi rigid foot bed including a foot plate contoured to underlie at least a portion of a foot of the wearer, a cut out portion configured to receive a heel of the wearer, a medial wing extending generally upward from a posterior medial edge of the foot plate, and a lateral wing extending generally upward from a posterior lateral edge of the foot plate, wherein the medial wing and the lateral wing each further comprise posterior extensions that are configured to provide calcaneal support to the wearer; wherein the foot bed is rotatably coupled to the ankle cuff; a medial bend region joining the medial wing to the foot plate and a lateral bend region joining the lateral wing to the foot plate, and wherein the foot plate is more rigid than the medial bend region and the lateral bend region; and
a removably attached liner.

2. The ankle brace of claim 1, wherein the foot bed is configured to fit within a shoe of the wearer.

3. The ankle brace of claim 1, wherein the ankle cuff is constructed of a heat-moldable material.

4. The ankle brace of claim 1, wherein the foot plate is configured to underlie the foot of the wearer over an area spanning a width of the wearer's foot and configured to extend from adjacent a ball of the wearer's foot to adjacent the heel of the foot.

5. The ankle brace of claim 1, wherein the liner comprises padding removably attached to the ankle cuff.

6. The ankle brace of claim 5, wherein the liner comprises an Achilles pad configured to cover an Achilles heel of a wearer.

7. The ankle brace of claim 5, further comprising an outer sleeve configured to be disposed over an ankle joint of a wearer.

8. The ankle brace of claim 7, wherein the outer sleeve is further configured to surround a forward edge of the foot bed.

9. The ankle brace of claim 1, further comprising at least one semi-rigid strap extending from the calf-supporting portion and including a ratchet mechanism to adjustably position the ankle cuff.

10. The ankle brace of claim 9, wherein at least a part of the strap is formed integrally with the calf-supporting portion.

11. The ankle brace of claim 9, wherein the at least one semi-rigid strap comprises:
a medial strap extending forward from the medial side of the calf-supporting portion and
a lateral strap extending forward from the lateral side of the calf-supporting portion; and
wherein the medial strap and the lateral strap are configured to mate such that a circumference of the ankle cuff is incrementally adjustable.

12. The ankle brace of claim 11, wherein the ratchet mechanism provides incremental adjustability.

* * * * *